(12) United States Patent
Nozue

(10) Patent No.: US 6,866,627 B2
(45) Date of Patent: Mar. 15, 2005

(54) ENDOSCOPE DISTAL HOOD COMPONENT

(75) Inventor: Kota Nozue, Hachioji (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 10/680,461

(22) Filed: Oct. 7, 2003

(65) Prior Publication Data

US 2004/0073089 A1 Apr. 15, 2004

(30) Foreign Application Priority Data

Oct. 11, 2002 (JP) ........................................ 2002-299350

(51) Int. Cl.[7] .............................................. A61B 1/00
(52) U.S. Cl. ...................................... 600/127; 600/129
(58) Field of Search ................................ 600/121–127, 600/129, 153

(56) References Cited

U.S. PATENT DOCUMENTS

| 6,306,081 | B1 | * | 10/2001 | Ishikawa et al. | ............ | 600/127 |
| 6,524,234 | B2 | * | 2/2003 | Ouchi | ........................ | 600/127 |
| 2003/0088154 | A1 | * | 5/2003 | Ishibiki et al. | .............. | 600/127 |
| 2003/0225312 | A1 | * | 12/2003 | Suzuki et al. | ................ | 600/114 |

FOREIGN PATENT DOCUMENTS

| JP | 59-15605 | 5/1984 |
| JP | 59-93413 | 5/1984 |
| JP | 2001-224550 | 8/2001 |
| JP | 2002-301010 | 10/2002 |
| JP | 2003-245244 | 9/2003 |

OTHER PUBLICATIONS

Uno, Y., "Discussion on Safety of Slim Colonoscope CF–SV", Journal of Japanese Society of Medical Instrumentation vol. 67, No. 7 (supplementary volume), p. 289–292, Jul. 1, 1997.

* cited by examiner

Primary Examiner—Beverly M. Flanagan
(74) Attorney, Agent, or Firm—Scully, Scott, Murphy & Presser

(57) ABSTRACT

With respect to an endoscope distal hood component of the present invention, a protrusion of a distal hood component fitted to the distal end of an endoscope is formed to be elastically deformable in order that when this protrusion is pressed against an observation target, the protrusion is deformed due to an external force at that time, and a part thereof is entered into the range of the observational field of view. Since a part of the protrusion is entered into the range of the observational field of view, the surgeon becomes aware that the protrusion is pressed against the observation target, and does not further press the protrusion against the observation target.

19 Claims, 3 Drawing Sheets

ENDOSCOPE DISTAL HOOD COMPONENT

This application claims benefits of Japanese Patent Application No. 2002-299350 filed on Oct. 11, 2002, in Japan, the entire contents of which are hereby incorporated by reference.

BACKGROUND OF THE INVENTION

1. Field of the Invention

The present invention relates to an endoscope distal hood component provided at an insertion portion distal end of an endoscope in order to ensure a closest approach distance between the insertion portion distal end of the endoscope and a subject.

2. Description of the Related Art

An example of conventional endoscope apparatuses used for surgery is formed to be provided with an observational optical system, a light guide, an air and water feed hole and a suction hole at the distal end of the insertion portion of the endoscope.

With respect to such an endoscope apparatus, illumination light is applied to a subject, e.g., living body tissue, from a light guide, and operations, e.g., suction of air, water, or other substance fed from the air and water feed hole with the suction hole, are performed while the reflected light from the subject is visually identified through an objective lens.

On the other hand, with respect to some endoscopes, a hood component is provided at an insertion portion distal end of the endoscope in order to ensure a closest approach distance between an observation window of an observational optical system and a subject. For example, Japanese Examined Utility Model Registration Application Publication No. 59-15605 discloses a hood component which is freely detachably provided at a distal end of an insertion portion of an endoscope and which is formed into the shape of a substantially regular cylinder.

According to the technology disclosed in this publication, the hood component is fitted to the insertion portion distal end of the endoscope, the endoscope observation is performed while the distal end of the hood component is in contact with the subject and, thereby, the distance between the subject and the end surface of the distal end at which a first lens surface of the objective optical system is located can be maintained constant, so that the observation of an easy-to-move subject, e.g., a mucosa, can be easily performed.

Japanese Unexamined Patent Application Publication No. 2001-224550 discloses a technology in which a substantially cylindrical hood component provided at an insertion portion distal end of an endoscope is formed into the shape not included within the range of the observational field of view.

SUMMARY OF THE INVENTION

An endoscope distal hood component of the present invention includes a protrusion which is integrally or detachably provided at a distal end of the insertion portion of an endoscope to be inserted into a lumen and which is protruding in the direction of the observational field of view of the above-described endoscope, wherein the protrusion has the shape which is not included within the above-described range of the observational field of view, the protrusion is made from an elastically deformable soft component, and the protrusion is formed in order that when the protrusion is deformed by an external force from the direction of the distal end or the side, the deformed portion is entered into the above-described range of the observational field of view.

The above and other objects, features and advantages of the invention will become more clearly understood from the following description referring to the accompanying drawings.

BRIEF DESCRIPTION OF THE DRAWINGS

FIG. 1 is a perspective view of an endoscope distal end fitted with a distal hood component.

FIG. 2 is a diagram for explaining an external force applied from a target to the distal hood component.

FIG. 3 is a diagram for explaining deformation due to the application of the external force to the distal hood component.

FIG. 4 is a diagram for explaining the distal end surface of the distal hood component.

FIG. 5 is a diagram for explaining a force applied from a target to a distal hood component.

FIG. 6 is a diagram for explaining deformation due to the external force applied to the distal hood component.

DESCRIPTION OF THE PREFERRED EMBODIMENTS

FIG. 1 to FIG. 4 show the first embodiment of the present invention.

Figure 1:
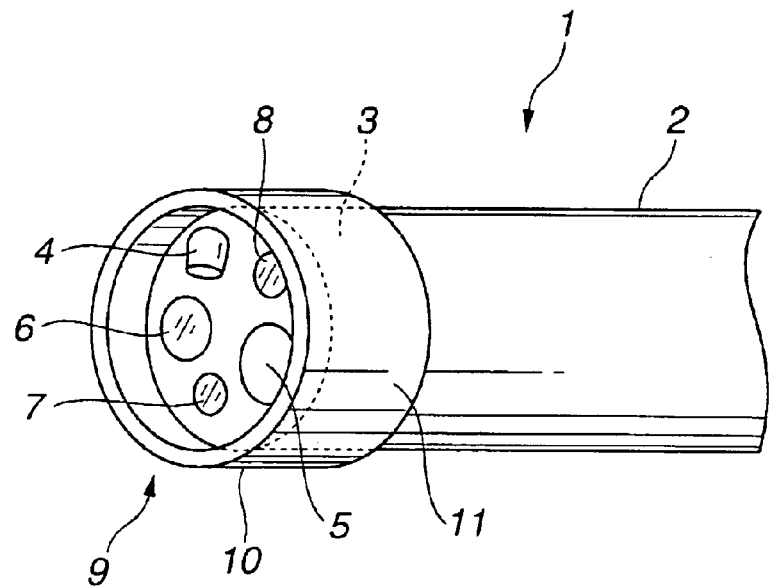
FIG. 1 to FIG. 4 show a first embodiment of the present invention.

As shown in FIG. 1, an endoscope 1 constitutes an endoscope apparatus together with a light source device, a video processor and a monitor, although not shown in the drawing.

An air and water feed nozzle 4 which is a hole for feeding air and water, a suction hole 5, an observational optical system 6 and illumination windows 7 and 8 are provided on the end surface of a distal end 3 of an insertion portion 2 of the endoscope 1. The observational optical system 6 includes objective lenses, and a front-end lens of the objective lenses is arranged at the observation window. Although not shown in the drawing, an image entry surface (in the case of an electronic endoscope, an image pickup surface of a solid-state image pickup device) of an image fiber bundle is arranged in the endoscope base end surface side of the objective lenses. An output surface of the light guide fiber bundle is arranged inside the observation windows 7 and 8.

On the other hand, a distal hood component 9 is freely detachably provided at the distal end 3 of this endoscope 1. The distal hood component 9 is formed from an elastically deformable soft component, for example, vulcanized rubber, e.g., silicon rubber and fluororubber; thermoplastic elastomers, e.g., urethane-based elastomers, acrylic elastomers and olefin-based elastomers, and the like.

This distal hood component 9 is formed to have a substantially cylindrical shape, and includes a protrusion 10 protruding from the distal end 3 side and an endoscope fixation portion 11 into which the distal end 3 is fitted. This endoscope fixation portion 11 is fixed to the distal end 3 by press fitting. In this case, the distal hood component 9 may be integrated with the distal end 3.

Figure 2:
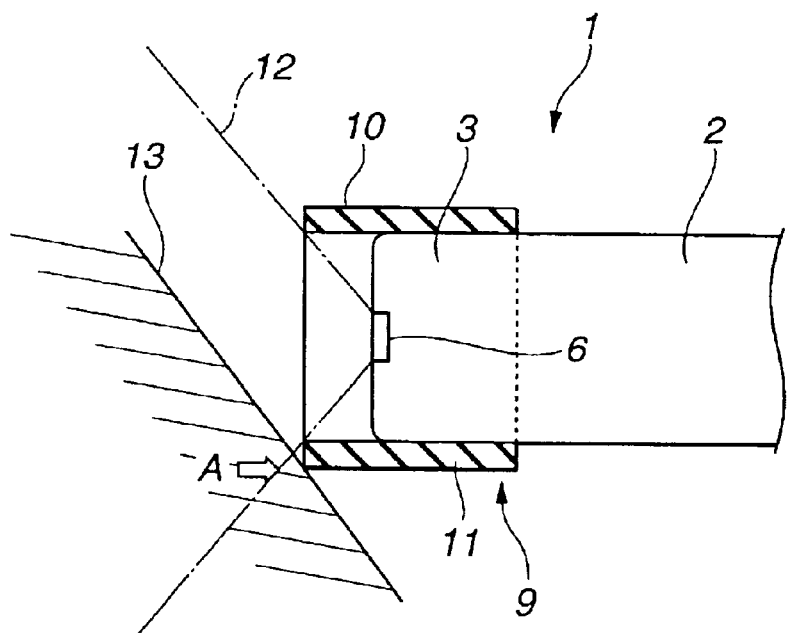

As shown in FIG. 2, the protrusion 10 provided in the distal hood component 9 is formed to have the shape which is not included within the range 12 of the observational field of view of the observational optical system 6 while the protrusion 10 is not deformed. The basic shape of the protrusion 10 is a substantially cylindrical shape. Consequently, with respect to the structure, the protrusion is unlikely to be deformed in the direction of the outer perimeter, but is likely to be deformed in the direction of the inner perimeter when an external force is applied from the direction of the distal end or the side.

As shown in FIG. 2, this distal end is adjusted to deform by a force of 0.29 MPa or less in the case where an external force indicated by an arrow A is applied from an observation target 13 side to the end of the protrusion 10.

Figure 3:
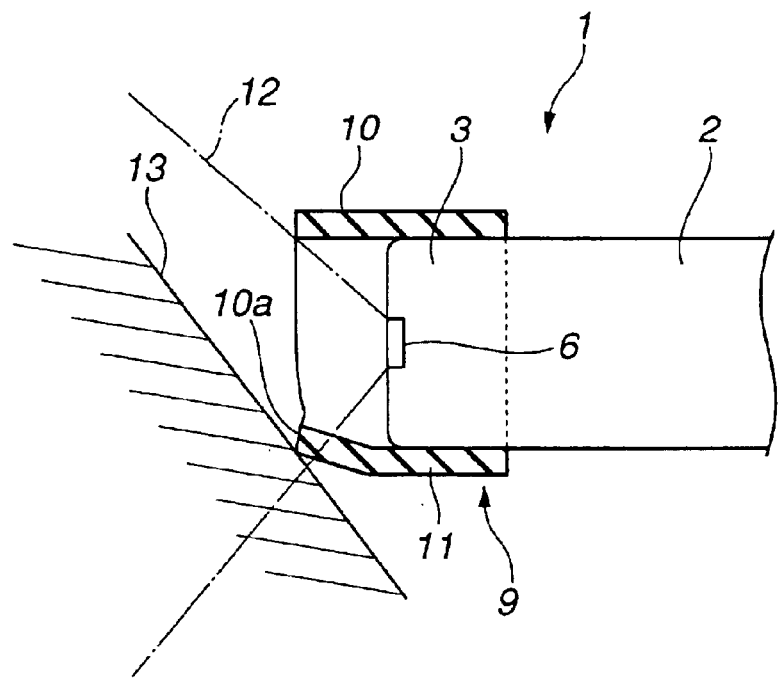

Furthermore, as shown in FIG. 3, the protrusion 10 is formed to have the shape in which the protrusion 10 is deformed in the direction of the inner perimeter when an external force is applied from the direction of the distal end or the side, and a part of the deformed portion 10a is entered into the range 12 of the observational field of view of the observational optical system 6.

Figure 4:
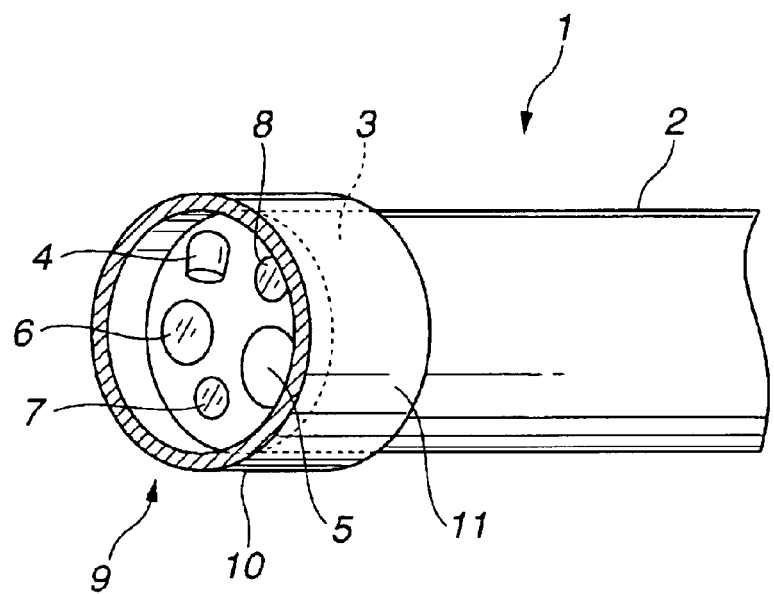

Here, as shown in FIG. 4, the area of the distal end surface (the area of the diagonally shaded portion) of the protrusion 10 in contact with the observation target 13 is represented by S, and a pressure applied to this area S is represented by P. As shown in FIG. 2, when the external force is applied to the distal end surface of the protrusion 10, an applied force F is represented by the following formula.

$$F = P \times S \quad (1)$$

The case where the protrusion 10 is formed to deform at a pressure P of 0.2 MPa (2 kgf/cm$^2$) is discussed.

For example, when S=0.4 [cm$^2$], the shape, dimensions and the material of the protrusion 10 of the distal hood component 9 are adjusted in order that the protrusion 10 is deformed at a force F=0.8 kgf which is applied to the distal end surface of the protrusion 10 and which is determined based on the formula (1).

For example, when S=0.3 [cm$^2$], the shape, dimensions and the material of the protrusion 10 of the distal hood component 9 are adjusted in order that the protrusion 10 is deformed at an applied force F=0.6 kgf determined based on the formula (1).

According to such a configuration, when an external force is applied to the protrusion 10 from the distal end side, the protrusion 10 is deformed in the direction of the inner perimeter and, thereby, the external force can be relieved. In this manner, the stress does not concentrate on the protrusion 10 and the endoscope fixation portion 11 and, therefore, damage to the protrusion 10 can be prevented from occurring without adopting an expensive material for the distal hood component 9.

With respect to a structure in which the endoscope fixation portion 11 provided in the distal hood component 9 is fixed to the distal end 3 of the endoscope 1 by press fitting as well, the external force is relieved by deformation of the protrusion 10 and, thereby, no strain is applied to the endoscope fixation portion 11. Consequently, this endoscope fixation portion 11 is not displaced or detached from the distal end 3, so that simplification of the fixation structure can be realized.

A publication in Japan, Yoshiharu Uno, "Saikei daichou naishikyou CF-SV no anzenseino kentou (Discussion on safety of slim colonoscope CF-SV)", Japanese journal of medical instrumentation, 67, No. 7 bessatsu (supplementary volume), issued on Jul. 1, 1997, p.289–292, discloses that application of a force of 3 to 4 kg/cm$^2$ or more to an intestinal paries causes perforation of the intestinal paries with a high possibility in theory.

Consequently, the surgeon must operate the endoscope in order that a force of more than or equal to the above-described value is not applied to the intestinal paries, that is, a force of 3 to 4 kg/cm$^2$ or more is not applied to the protrusion 10.

In the present embodiment, when the protrusion 10 is pressed against a mucosa during an inspection using the endoscope, the protrusion 10 is deformed at 0.2 MPa. That is, deformation reliably occurs at about 0.29 MPa (3 kgf/cm$^2$) or less. Since the surgeon performs operations in order that such a force is not applied, damage to the protrusion 10 and the endoscope fixation portion 11 can be prevented from occurring.

Furthermore, when the protrusion 10 is pressed against a mucosa of the observation target 13, the protrusion 10 is deformed, and a part of the deformed portion 10a is entered into the range 12 of the observational field of view. In this manner, the surgeon can become aware that the protrusion 10 is deformed before a force of about 0.29 MPa or more (3 kgf/cm$^2$ or more) is applied to the protrusion 10.

As described above, according to the present embodiment, since the distal hood component 9 is used, the observational field of view can be easily ensured, and an improvement in the observational performance can be realized.

Since the protrusion 10 is adjusted to deform by a force of 0.29 MPa or less, application of an excessive force to the distal hood component 9 can be prevented. Therefore, damage to the distal hood component 9 can be prevented from occurring, and an improvement in the durability can be achieved without using an expensive material.

Since the protrusion 10 is deformed by a force of 0.29 MPa or less, the patient can have a reduced uncomfortable feeling. Furthermore, when an external force is applied to the protrusion 10 from the direction of the distal end or the side, the distal end is deformed to enter into the range 12 of the observational field of view. Consequently, the surgeon can become aware that the protrusion 10 is deformed before a force of about 0.29 MPa or more (3 kgf/cm$^2$ or more) is applied to the protrusion 10. Therefore, the distal end 3 of the endoscope 1 is not pressed against the observation target 13 with a force of more than or equal to that, and the endoscope observation can be performed while the distance between the observation target 13 and the distal end 3 of the endoscope 1 is maintained constant.

Figure 5:
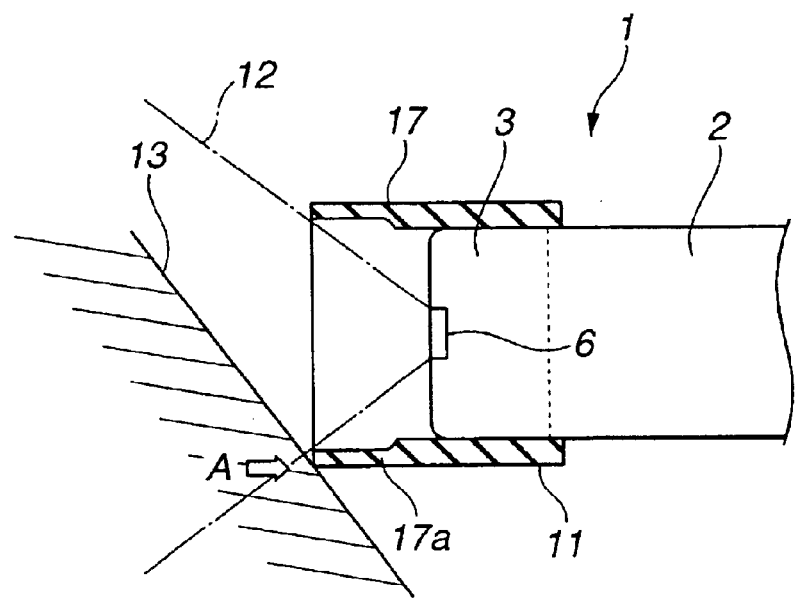
FIG. 5 and FIG. 6 show a second embodiment of the present invention.
Figure 6:
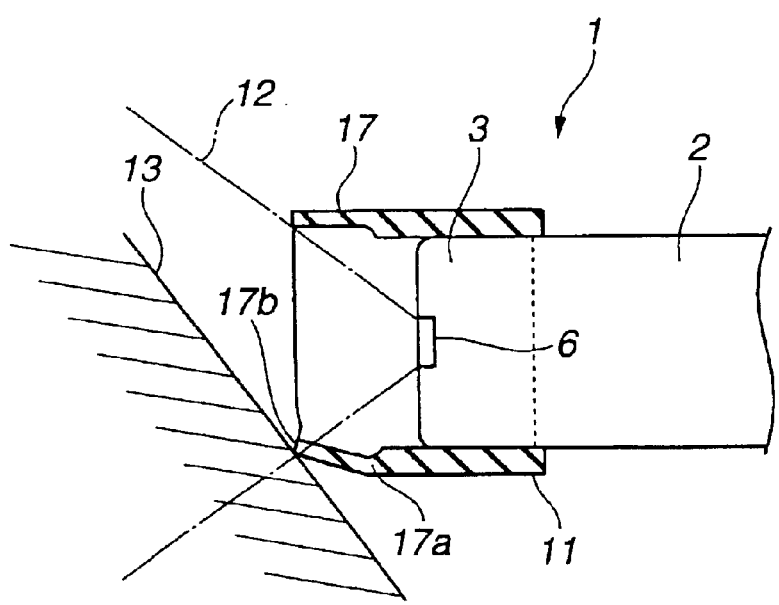

FIG. 5 and FIG. 6 show the second embodiment of the present invention.

As shown in FIG. 5, an endoscope 1 according to the present embodiment has a configuration similar to that in the above-described first embodiment, and only the configuration of the distal hood component 16 is different. The material of the distal hood component 16 is similar to that of the distal hood component 9 in the first embodiment.

The protrusion 17 of the distal hood component 16 is provided with a distal thin-walled portion 17a having a thickness smaller than that of the base end side of the protrusion 17 in order that deformation is likely to occur when an external force is applied from the distal end side of this protrusion 17. This distal thin-walled portion 17a is adjusted to deform by a force of 0.29 MPa or less in a manner similar to that of the protrusion 10 in the first embodiment.

According to such a configuration, as shown in FIG. 6, when an external force is applied to the protrusion 17 from the distal end side, the distal thin-walled portion 17a is deformed in the direction of the inner perimeter and, thereby, the external force is relieved. In this manner, the stress does not concentrate on the protrusion 17 and the endoscope fixation portion 11 and, therefore, damage to the protrusion 17 can be prevented from occurring even when an inexpensive material is used for the distal hood component 16.

With respect to a structure in which the endoscope fixation portion 11 of the distal hood component 16 is fixed to the distal end 3 of the endoscope 1 by press fitting as well, the endoscope fixation portion 11 is not displaced or detached from the distal end 3, so that ease of operation is achieved.

Furthermore, when the protrusion 17 is pressed against a mucosa of the observation target 13, the distal thin-walled portion 17a of the protrusion 17 is deformed, and a part of the deformed portion 17b is entered into the range 12 of the observational field of view. Consequently, the surgeon can become aware that the protrusion 17 is deformed before the protrusion 17 is pressed against an intracavital paries surface by a force of about 0.29 MPa or more (3 kgf/cm² or more) in a manner similar to that in the above-described first embodiment, and the protrusion 17 is not pressed against the intracavital paries surface with a force of more than or equal to that. Therefore, the patient can have a significantly reduced uncomfortable feeling.

As described above, according to the present embodiment, since the distal hood component 16 is used, the observational field of view can be easily ensured, and an excellent observational performance can be achieved.

Since the distal thin-walled portion 17a of the protrusion 17 is adjusted to deform by a force of 0.29 MPa or less, application of an excessive force to the distal hood component 16 can be prevented. Therefore, damage to the distal hood component 16 can be prevented from occurring, and an improvement in the durability can be achieved without using an expensive material.

Since the distal thin-walled portion 17a of the protrusion 17 is adjusted to deform by a force of 0.29 MPa or less, when the protrusion 17 is pressed against the intracavital paries surface, a force of more than or equal to that is not applied. Consequently, the patient can have a reduced uncomfortable feeling.

Furthermore, when an external force is applied to the distal thin-walled portion 17a of the protrusion 17 from the direction of the distal end or the side, the distal end is deformed to enter into the range 12 of the observational field of view. Consequently, the surgeon can become aware that the protrusion 17 is deformed before a force of about 0.29 MPa or more (3 kgf/cm² or more) is applied to the protrusion 17.

The observational field of view can be easily ensured because of the distal hood component, and an improvement in the observational performance can be achieved.

As described above, according to each embodiment, since the protrusion provided in the distal hood component is formed to have a capability to deform by an external force from the distal end side, application of an excessive force to the distal hood component can be prevented. Therefore, damage to the distal hood component can be prevented from occurring, and an improvement in the durability can be achieved without using an expensive material. In addition, the patient can have a reduced uncomfortable feeling.

When a part of the protrusion is deformed, a part of the deformed portion is entered into the range of the observational field of view. Consequently, the surgeon can easily become aware of the deformation of the distal hood component, and the surgeon does not press with a further force, so that the patient can have a significantly reduced uncomfortable feeling.

The present invention is not limited to the above-described each embodiment. For example, other structures may be adopted, as long as the protrusions 10 and 17 of the distal hood components 9 and 16 are formed to easily deform in the direction of the inner perimeter, and the distal ends thereof are configured to enter into the range 12 of the observational field of view of the observational optical system when these protrusion 10 and 17 are deformed.

The protrusions 10 and 17 of the distal hood components 9 and 16 are not limited to have the shape of a cylinder. The cross-sectional shape of the total protrusions 10 and 17 may be an ellipse, a rectangle, a shape having a partial linear portion, and a tubular shape having a polygonal shape, e.g., a substantially tetragonal shape and a substantially octagonal shape.

Furthermore, the distal hood components 9 and 16 may be freely attached to or detached from the distal end 3 of the endoscope 1, or be integrally formed with the distal end 3 of the endoscope 1 while being impossible to attach and detach.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope distal hood component comprising a protrusion provided at a distal end of the insertion portion of an endoscope to be inserted into a lumen, wherein the protrusion is protruding in the direction of the observational field of view of the endoscope, wherein the protrusion has the shape which is not included within the range of the observational field of view, wherein the protrusion is made from an elastically deformable soft component, wherein the protrusion is formed in order that when the protrusion is deformed by an external force from the direction of the distal end or the side, the deformed portion is entered into the range of the observational field of view, and wherein the protrusion which is deformable is continuously formed along a circumference thereof.

2. The endoscope distal hood component according to claim 1, wherein the protrusion is integrally provided at the distal end of the insertion portion of the endoscope.

3. The endoscope distal hood component according to claim 1, wherein the protrusion is freely detachably provided at the distal end of the insertion portion of the endoscope.

4. The endoscope distal hood component according to claim 1, wherein the protrusion is provided to deform by an external force of about 0.29 MPa or less.

5. The endoscope distal hood component according to claim 2, wherein the protrusion is provided to deform by an external force of about 0.29 MPa or less.

6. The endoscope distal hood component according to claim 3, wherein the protrusion is provided to deform by an external force of about 0.29 MPa or less.

7. The endoscope distal hood component according to claim 1, wherein the distal end side of the protrusion is made of a thin-walled portion having a thickness smaller than that of the base end side.

8. The endoscope distal hood component according to claim 2, wherein the distal end side of the protrusion is made of a thin-walled portion having a thickness smaller than that of the base end side.

9. The endoscope distal hood component according to claim 3,
wherein the distal end side of the protrusion is made of a thin-walled portion having a thickness smaller than that of the base end side.

10. The endoscope distal hood component according to claim 4,
wherein the distal end side of the protrusion is made of a thin-walled portion having a thickness smaller than that of the base end side.

11. The endoscope distal hood component according to claim 5,
wherein the distal end side of the protrusion is made of a thin-walled portion having a thickness smaller than that of the base end side.

12. The endoscope distal hood component according to claim 6,
wherein the distal end side of the protrusion is made of a thin-walled portion having a thickness smaller than that of the base end side.

13. The endoscope distal hood component according to claim 7,
wherein the thin-walled portion is provided in order that the thin-walled portion is deformed by an external force from the direction of the distal end or the side, and is entered into the range of the observational field of view.

14. The endoscope distal hood component according to claim 8,
wherein the thin-walled portion is provided in order that the thin-walled portion is deformed by an external force from the direction of the distal end or the side, and is entered into the range of the observational field of view.

15. The endoscope distal hood component according to claim 9,
wherein the thin-walled portion is provided in order that the thin-walled portion is deformed by an external force from the direction of the distal end or the side, and is entered into the range of the observational field of view.

16. The endoscope distal hood component according to claim 10,
wherein the thin-walled portion is provided in order that the thin-walled portion is deformed by an external force from the direction of the distal end or the side, and is entered into the range of the observational field of view.

17. The endoscope distal hood component according to claim 11,
wherein the thin-walled portion is provided in order that the thin-walled portion is deformed by an external force from the direction of the distal end or the side, and is entered into the range of the observational field of view.

18. The endoscope distal hood component according to claim 12,
wherein the thin-walled portion is provided in order that the thin-walled portion is deformed by an external force from the direction of the distal end or the side, and is entered into the range of the observational field of view.

19. The endoscope distal hood component according to claim 1,
wherein the protrusion which is deformable has a single wall in thickness.

* * * * *